United States Patent [19]

Sheehan et al.

[11] 3,978,034
[45] Aug. 31, 1976

[54] L-ASPARTYL DIPEPTIDES AS SWEETENING AGENTS

[75] Inventors: John T. Sheehan, Middlesex; Miguel A. Ondetti, North Brunswick, both of N.J.

[73] Assignee: E. R. Squibb & Sons, Inc., Princeton, N.J.

[22] Filed: Nov. 12, 1969

[21] Appl. No.: 876,054

[52] U.S. Cl. .......................... 260/112.5 R; 426/548
[51] Int. Cl.² .................. C07C 103/52; A23L 1/22
[58] Field of Search .................................. 260/112.5

[56] References Cited
UNITED STATES PATENTS

| | | | |
|---|---|---|---|
| 3,475,403 | 10/1969 | Mazur et al. | 260/112.5 |
| 3,492,131 | 1/1970 | Schlatter | 99/141 |
| 3,642,491 | 2/1972 | Schlutter | 99/28 |

OTHER PUBLICATIONS

Mazur et al., J. Am. Chem. Soc. 91, pp. 2684–2691 (1969).

Gregory et al., J. Chem. Soc. 1968, c, pp. 531–540.

*Primary Examiner*—Lewis Gotts
*Assistant Examiner*—Reginald J. Suyat
*Attorney, Agent, or Firm*—Lawrence S. Levinson; Merle J. Smith

[57] ABSTRACT

Dipeptides of the formula:

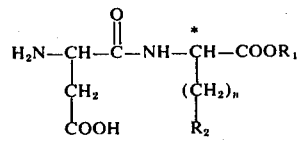

wherein $n$ is an integer from 0 to 5, $R_1$ is an alkyl, alkylaryl or alicyclic radical, and $R_2$ is a cycloalkenyl radical, and, in addition, may be phenyl when $n$ is 0. The carbon marked with an asterisk is always of the L-configuration. These compounds have a sweet taste and are useful as sweetening agents.

4 Claims, No Drawings

L-ASPARTYL DIPEPTIDES AS SWEETENING AGENTS

It is an object of the present invention to provide novel compounds. Another object is to provide novel sweetening agents. A further object is to provide a method for preparing these compounds. These and other objects will be apparent from the following description:

SUMMARY OF THE INVENTION

Compounds of the general formula:

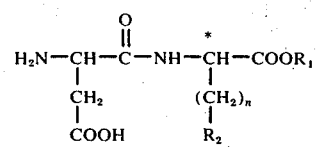

wherein $n$ is an integer from 0 to 5, $R_1$ is an alkyl radical of up to 6 carbon atoms, an alkylaryl or alicyclic radical of up to 10 carbon atoms, and $R_2$ is a cycloalkenyl radical, and, in addition, may be phenyl when $n$ is 0. The carbon marked with an asterisk is always of the L-configuration.

DETAILED DESCRIPTION

The new compounds of the present invention are dipeptides which possess a sweet taste. This property is useful in that these dipeptides are susceptible of imparting a sweet taste to various comestibles. Examples of some comestibles which may be sweetened by the use of the dipeptides of the present invention are: fruit, fruit juices, vegetables, salad seasonings, ice cream, sherbet, gelatin, syrups, pastry mixtures, wines, carbonated and noncarbonated beverages, chewing gum, and candy. The compounds of the present invention have a favorable ratio of sweetness to caloric content and may be used by themselves, or in combination with natural or artificial sweetening agents, such as, for example, sucrose or saccharin.

The dipeptide sweetening agents of the present invention are stable, water-soluble substances which may be utilized under various physical forms, for example, as powders, tablets, syrups, and so forth. They may also be used in liquid or solid carriers, such as, water, glycerin, sorbitol, starch, salt, citric acid and other appropriate non-toxic substances. While it is not possible to predict whether a given dipeptide structure will taste sweet or even have a taste at all, is has been determined that the sweet tasting property is influenced by the stereochemistry of the amino acids constituting the structure of the dipeptide. In order to obtain the maximum sweetening effect, the carbon atom marked with an asterisk in the general formula is always of the L-configuration.

The sweetening agents of the present invention are of particular interest as sugar substitutes for diabetics, obese persons, and persons under controlled caloric intake. Moreover, they do not possess the disagreeable aftertaste which is present in synthetic sweeteners. As derivatives of amino acids utilized in the human organism in the synthesis of essential proteins, they are free of toxic properties.

In the compounds of the present invention, the radical $R_1$ may be an alkyl radical of up to 6 carbon atoms, an alkyl-aryl or alicyclic radical of up to 10 carbon atoms. The alkyl chain may be straight or branched. Examples of such alkyl radicals are the following: methyl, ethyl, n-propyl, i-propyl, n-butyl, i-butyl, n-pentyl, 2-methylbutyl, neopentyl, n-hexyl, 2-methylpentyl, 3-methylpentyl, 2,2-dimethylbutyl and 2,3-dimethylbutyl. Examples of alkyl-aryl radicals are benzyl, phenethyl, isopropylphenyl, 3-phenylpropyl and isopropylbenzyl. Examples of alicyclic radicals are cyclopropyl, cyclobutyl, cyclopentyl, cyclohexyl, cycloheptyl and cyclooctyl. $R_2$ may be a mono or diunsaturated alicyclic radical of up to 8 carbon atoms, and, in addition, may be phenyl when $n$ is 0. Examples of specific alicyclic radicals are the following: cyclopropenyl, cyclobutenyl, cyclopentenyl, cyclohexenyl, cycloheptenyl, cyclooctenyl, cyclobutadienyl, cyclopentadienyl, cyclohexadienyl, cycloheptadienyl and cyclooctadienyl.

The following examples illustrate the present invention without, however, limiting the same thereto:

EXAMPLE 1

2,5-Dihydro-L-phenylalanine methyl ester hydrochloride

Thionyl chloride (15 ml.) is added to methanol (150 ml.) while stirring in a dry ice bath. The mixture is allowed to come to room temperature and 2,5-dihydro-L-phenylalanine (5.0 g.) is added. After refluxing for 30 minutes, the solvent is removed in vacuo and the residue is crystallized from ether and then recrystallized from acetonitrile. Yield: 4.95 g.

EXAMPLE 2

β-Tert.butyl-N$^\alpha$-tert.-butyloxycarbonyl-L-aspartyl-2,5-dihydro-L-phenylalanine methyl ester β-tert.-butyl-N$^\alpha$-tert.-butyloxycarbonyl-L-aspartic acid p-nitrophenyl ester (26.7 g.) is added to a mixture of 2,5-dihydro-L-phenylalanine methyl ester hydrochloride (11.8 g.), dimethylformamide (50 ml.) and triethylamine (7.6 ml.). After two hours at room temperature the reaction mixture is diluted with ethyl acetate and washed with 20% aqueous citric acid, water, saturated sodium bicarbonate and water. After drying over magnesium sulfate the solvent is removed in vacuo. Yield: 13.2 g.

EXAMPLE 3

L-Aspartyl-2,5-dihydro-L-phenylalanine methyl ester

β-tert.-butyl-N$^\alpha$-tert.-butyloxycarbonyl-L-aspartyl-2,5-dihydro-L-phenylalanine methyl ester (13 g.) is dissolved in trifluoroacetic acid (80 ml.) and the solution kept under nitrogen for one hour. The solvent is concentrated in vacuo and the residue is triturated with ether-hexane until it becomes solid. This material is dissolved in water (ca 30 ml.) neutralized with DEAE sephadex (OH cycle), filtered and the filtrate concentrated in vacuo to a small, volume (ca 5 ml.). The dipeptide ester is crystallized on standing in the refrigerator.

EXAMPLE 4

1-Cyclohexene-1-L-alanine methyl ester hydrochloride

Prepared from 1-cyclohexene-1-L-alanine as described in Example 1.

EXAMPLE 5

β-Tert.-butyl-N$^\alpha$-tert.-butyloxycarbonyl-L-aspartyl-L-(1-cyclohexene-1)-alanine methyl ester Prepared from 1-cyclohexene-1-L-alanine methyl ester hydrochloride as described in Example 2.

EXAMPLE 6

L-Aspartyl-L-(1-cyclohexene-1)-alanine methyl ester

Prepared from the protected dipeptide of Example 5 by the procedure described in Example 3.

EXAMPLE 7

β-Benzyl-N$^\alpha$-tert.-butyloxycarbonyl-L-aspartyl-L-phenylglycine

β-benzyl-N$^\alpha$-tert.-butyloxycarbonyl-L-aspartic acid p-nitrophenyl ester (5.3 g.) is added to a mixture of L-phenyl glycine (1.5 g.), triethylamine (1.4 ml.) and dimethylformamide (15 ml.). After overnight standing at room temperature the reaction mixture is diluted with ethyl acetate, washed with 20% citric acid and water. After drying over magnesium sulfate the solvent is removed in vacuo and the residue is crystallized as a dicyclohexylammonium salt. Yield: 3.6 g.

EXAMPLE 8

L-Aspartyl-L-phenylglycine methyl ester

β-benzyl-N$^\alpha$-tert.-butyloxycarbonyl-L-aspartyl-L-phenylglycine dicyclohexyl-ammonium salt (3 g.) is dissolved in a mixture of ethyl acetate (200 ml.) and 20% aqueous citric acid (50 ml.). The organic layer is washed twice with water, dried over magnesium sulfate, and concentrated to dryness in vacuo. The residue is dissolved in methanol, treated with diazomethane until a permanent yellow color is obtained. The color is discharged after ten minutes with a drop of acetic acid, and the solvent is removed in vacuo. The residue is dissolved in absolute ethanol (100 ml.) and hydrogenated with a catalyst of 10% palladium on charcoal at atmospheric pressure for 5 hours. The catalyst is filtered off and the filtrate concentrated to dryness in vacuo. The residue is dissolved in trifluoroacetic acid (10 ml.) and after 15 minutes at room temperature, the trifluoroacetic acid is removed in vacuo and the dipeptide methyl ester isolated as described in Example 3. Yield: 0.9 g.

EXAMPLE 9

L-2,5-dihydrophenylglycine methyl ester hydrochloride

Prepared from L-2,5-dihydrophenylglycine as described in Example 1.

EXAMPLE 10

β-Tert.-butyl-N$^\alpha$-tert.-butyloxycarbonyl-L-aspartyl-L-2,5-dihydrophenylglycine methyl ester Prepared from L-2,5-dihydrophenylglycine methyl ester hydrochloride as described in Example 2.

EXAMPLE 11

L-Aspartyl-L-2,5-dihydrophenylglycine methyl ester

Prepared from the protected dipeptide of Example 10, as described in Example 3.

What is claimed is:

1. A dipeptide of the formula

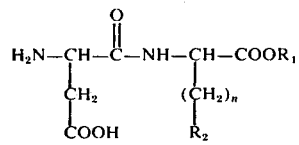

wherein each amino acid is of the L-configuration, $n$ is an integer from 0 to 5, $R_1$ is an alkyl radical of up to 6 carbon atoms, and $R_2$ is a mono- or diunsaturated cycloalkyl radical of up to 8 carbon atoms.

2. A dipeptide having the name L-aspartyl-2,5-dihydro-L-phenylalanine methyl ester.

3. A dipeptide having the name L-aspartyl-L-(1-cyclohexene-1)-alanine methyl ester.

4. A dipeptide having the name L-aspartyl-L-2,5-dihydrophenylglycine methyl ester.

* * * * *